United States Patent
Tsushima et al.

[11] Patent Number: 5,661,144
[45] Date of Patent: Aug. 26, 1997

[54] CEPHEM DERIVATIVES WITH 3-SUBSTITUTED BIS HETEROCYCLES

[75] Inventors: Masaki Tsushima; Kunio Atsumi; Katsuyoshi Iwamatsu; Atsushi Tamura, all of Yokohama, Japan

[73] Assignee: Meiji Seika Kabushiki Kaisha, Tokyo, Japan

[21] Appl. No.: 628,705
[22] PCT Filed: Aug. 16, 1995
[86] PCT No.: PCT/JP95/01627
§ 371 Date: Jun. 28, 1996
§ 102(e) Date: Jun. 28, 1996
[87] PCT Pub. No.: WO96/05205
PCT Pub. Date: Feb. 22, 1996

[30] Foreign Application Priority Data

Aug. 16, 1994 [JP] Japan ............... 6-192580

[51] Int. Cl.$^6$ ............... A61K 31/545; C07D 519/00
[52] U.S. Cl. ............... 514/202; 514/200; 540/222; 540/225
[58] Field of Search ............... 514/200, 202; 540/222, 225

[56] References Cited

U.S. PATENT DOCUMENTS

| | | | |
|---|---|---|---|
| 5,541,318 | 7/1996 | Aszodi et al. | 540/222 |
| 5,574,154 | 11/1996 | Abu-Nasrieh | 540/222 |
| 5,583,216 | 12/1996 | Ochiai et al. | 540/226 |
| 5,593,984 | 1/1997 | Lee et al. | 514/202 |

FOREIGN PATENT DOCUMENTS

| | | |
|---|---|---|
| 0315518 A1 | 5/1989 | European Pat. Off. . |
| 0329785 A1 | 8/1989 | European Pat. Off. . |
| 0551034 A3 | 7/1993 | European Pat. Off. . |
| 0551034 A2 | 7/1993 | European Pat. Off. . |
| 2684994 A1 | 6/1983 | France . |
| 2684995 A1 | 6/1993 | France . |
| 61-286388 | 12/1986 | Japan . |
| 2134522 | 8/1984 | United Kingdom . |
| 2157293 | 10/1985 | United Kingdom . |
| WO95/07912 | 3/1995 | WIPO . |

Primary Examiner—Mukund J. Shah
Assistant Examiner—Pavanaram K. Sripada
Attorney, Agent, or Firm—Wenderoth, Lind & Ponack

[57] ABSTRACT

Compounds represented by the following formula (I), that is, cephem derivatives having substituted or unsubstituted 3-(imidazo[5,1-b]thiazolium-6-yl)-1-propenyl as a substituent at the 3-position of the cephem ring:

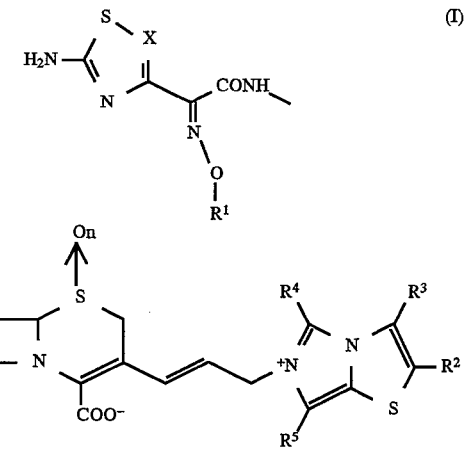

8 Claims, No Drawings

CEPHEM DERIVATIVES WITH 3-SUBSTITUTED BIS HETEROCYCLES

BACKGROUND OF THE INVENTION

1. Field of the Invention

The present invention relates to cephem derivatives having antibacterial activity effective against a wide spectrum of bacteria. More particularly, the present invention relates to novel cephem derivatives having substituted or unsubstituted imidazo[5,1-b]thiazolium-6-yl as a substituent at the 3-position of the cephem ring.

2. Background Art

Cephem antibiotics have excellent antibacterial activity with a low toxic for mammals. They are therefore remarkably effective in the treatment of infectious diseases in mammals. Those cephem derivatives which have an aminothiazolylacetyl group at the 7-position of the cephem ring have potent antibacterial activity and stability against beta-lactamase. For this reason, numerous studies and developments in these cephem derivatives have been made in recent years.

Onium-salt-type cephem antibiotics, such as ceftazidime and cefpirome, which have an aminothiazolylacetyl group at the 7-position and a quaternary salt substituent at the 3-position have potent antibacterial activity effective against a wide spectrum of bacteria from Gram-positive bacteria to *Pseudomonas aeruginosa*. Thus, numerous studies and developments in the antibiotics of this type have been made in many countries in the world. However, even the onium-salt-type cephem compounds such as ceftazidime and cefpirome may not be satisfactory in the antibacterial activity against *Pseudomonas aeruginosa* or Gram-positive bacteria such as *Staphylococcus aureus* which have brought about a clinical problem in recent years. In addition, infectious diseases caused by methicillin-resistant *Staphylococcus aureus* (MRSA) or penicillin-resistant *streptococcus pneumoniae* (PRSP) have been a serious clinical problem these days. It is therefore strongly demanded to obtain novel cephem antibiotics which have improved antibacterial activity also against these bacteria (W. E. Wick, "Cephalosporins and Penicillins, Chemistry and Biology" Chapter 11 edited by E. H. Flynn, Academic Press, New York, N.Y., 1972; 18.1 "Cephalosporins" by Hatsuo Aoki, "The Leading Studies in Antibiotics" edited by Masaji Oho and Satoshi Omura, Tokyo Kagaku Dojin Kabushiki Kaisha, Japan, 1987; and "Manifestation of Resistance and Molecular Genetics" by Ryoichi Okamoto and Matsuhisa Inoue, "*Sogo Rinsho*", Vol. 42, No. 2, 1993).

SUMMARY OF THE INVENTION

We now found cephem compounds which have an imidazo[5,1-b]thiazolium-6-yl structure at the 3-position having excellent antibacterial activity.

Thus, an object of the present invention is to provide novel cephem derivatives having potent antibacterial activity effective against a wide spectrum of bacteria.

Another object of the present invention is to provide pharmaceutical compositions comprising the novel cephem derivative of the present invention..

A further object of the present invention is to provide a method for treating infectious diseases comprising administering the novel cephem derivative of the present invention.

A still further object of the present invention is to provide use of the novel cephem derivative of the present invention for preparing an antibacterial agent.

Accordingly, compounds provided by the present invention are cephem derivatives represented by the following formula (I):

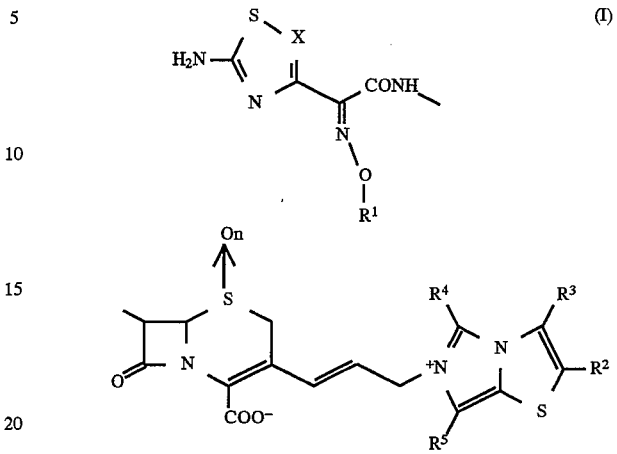

wherein

X represents CH or N, $R^1$ represents a hydrogen atom; $C_{1-4}$ alkyl in which one or more hydrogen atoms may be substituted by a group selected from a group consisting of halogen, hydroxyl, carboxyl, $C_{1-4}$ alkoxycarbonyl, carbamoyl, N—$C_{1-4}$ alkylcarbamoyl, cyano, amino and $C_{1-4}$ alkylamino; $C_{2-4}$ alkenyl; $C_{2-4}$ alkynyl; or $C_{3-6}$ cycloalkyl, $R^2$, $R^3$, $R^4$ and $R^5$, which may be the same or different, represent hydrogen; $C_{1-4}$ alkoxy; $C_{1-4}$ alkylthio; cyano; carboxyl; $C_{1-4}$ alkoxycarbonyl; carbamoyl; N—$C_{1-4}$ alkylcarbamoyl; formyl; amino in which one or more hydrogen atoms may be substituted by a group selected from a group consisting of formyl, $C_{1-4}$ alkylcarbonyl and $C_{1-4}$ alkylsulfonyl; halogen; $C_{1-4}$ alkyl in which one or more hydrogen atoms may be substituted by a group selected from a group consisting of hydroxyl, $C_{1-4}$ alkoxy, mercapto, $C_{1-4}$ alkylthio, cyano, halogen, carboxyl, $C_{1-4}$ alkoxycarbonyl, carbamoyl, N—$C_{1-4}$ alkylcarbamoyl, formyl, alkylcarbonyl, hydroxyimino, $C_{1-4}$ alkoxyimino, amino, formylamino, $C_{1-4}$ alkylcarbonylamino, $C_{1-4}$ alkylcarbonylamino (which may be substituted by a halogen atom), carbamoyloxy, N—$C_{1-4}$ alkylcarbamoyloxy, $C_{1-4}$ alkylsulfonylamino, ureido, N—$C_{1-4}$ alkylureido, $C_{1-4}$ alkoxycarbonylamino and imino $C_{1-4}$ alkylamino; $C_{3-6}$ cycloalkyl, $C_{2-4}$ alkenyl group; or $C_{2-4}$ alkynyl, or any two of $R^2$, $R^3$, $R^4$ and $R^5$ may form $C_{3-6}$ alkylene where one or more methylene groups in this alkylene group may be substituted by —NH—, —O—, —S— or —CO—, and n is 0 or 1; and pharmaceutically acceptable salts thereof.

An antibacterial composition according to the present invention comprises a compound of formula (I) together with a pharmaceutically acceptable carrier.

The compounds of the formula (I) have potent antibacterial activity effective against a wide variety of Gram-positive and Gram-negative bacteria.

DETAILED DESCRIPTION OF THE INVENTION

In this disclosure, "a $C_{1-4}$ alkyl group" as a group or a part of a group means a straight or branched chain $C_{1-4}$ alkyl group. Specific examples of this group include methyl, ethyl, propyl, iso-propyl, n-butyl, iso-butyl, s-butyl and t-butyl. Further, "an alkylene group" means a divalent group derived from a straight or branched alkane chain by removing one hydrogen atom from each terminal end thereof. Further, "a halogen atom" means a fluorine, chlorine, bromine or iodine atom.

Preferable examples of the $C_{1-4}$ alkyl group represented by $R^1$ in the formula (I) include methyl, ethyl, propyl, 1-methylethyl, fluoromethyl, difluoromethyl, 2-fluoroethyl, 3-fluoropropyl, 2-hydroxyethyl, cyanomethyl, carbamoylmethyl, (S)-1-carboxyethyl and 1-carboxy-1-methylethyl. Preferable examples of the $C_{2-4}$ alkenyl group represented by $R^1$ include 2-propenyl. Preferable examples of the $C_{2-4}$ alkynyl group represented by $R^1$ include (N-formyl-N-methylamino)methyl, ureidomethyl, (carbamoyloxy)methyl, (N-methylcarbamoyloxy)methyl, 2-(carbamoyloxy)ethyl, (acetylamino)methyl, (trifluoroacetylamino)methyl, and (N-methylureido)methyl.

Further, it is also possible that any two of $R^2$, $R^3$, $R^4$ and $R^5$ may form a $C_{3-6}$ alkylene group to form a ring structure. Moreover, one or more methylene groups in this $C_{3-6}$ alkylene group may be substituted by —NH—, —O—, —S— or —CO—. Preferable examples of such a structure include one in which $R^2$ and $R^3$ form a propano group, and one in which $R^3$ and $R^4$ form a 1-oxo-2-azapropano group. The structures of these groups are as follows:

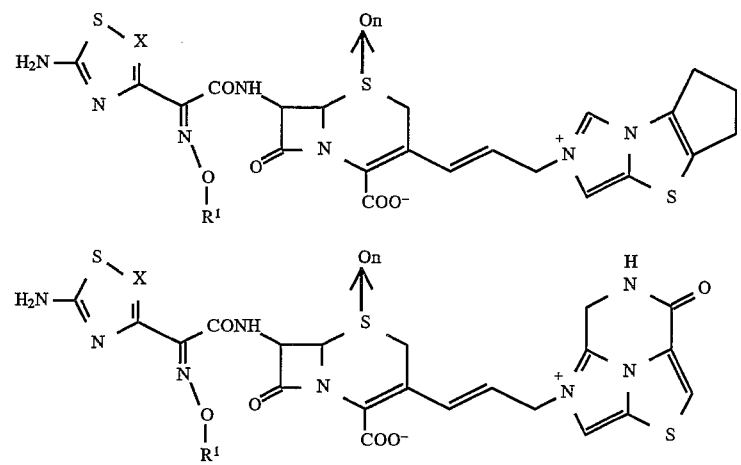

2-propynyl. Preferable examples of the $C_{3-6}$ cycloalkyl group represented by $R^1$ include cyclopentyl and cyclohexyl.

In the formula (I), $R^2$, $R^3$, $R^4$ and $R^5$ may be the same or different, and represent a $C_{1-4}$ alkoxy group (e.g., methoxy, ethoxy); a $C_{1-4}$ alkylthio group (e.g., methylthio); a cyano group; a carboxyl group; a $C_{1-4}$ alkoxycarbonyl group (e.g., methoxycarbonyl, ethoxycarbonyl); a carbamoyl group; an N—$C_{1-4}$ alkylcarbamoyl group (e.g., N-methylcarbamoyl, N-ethyl-carbamoyl); a formyl group; an amino group; a halogen atom; a $C_{1-4}$ alkyl group; a $C_{3-6}$ cycloalkyl group (e.g., cyclopentyl, cyclohexyl); a $C_{1-4}$ alkenyl group (e.g., 2-propenyl); or a $C_{2-4}$ alkynyl group (e.g., 2-propynyl). One or more hydrogen atoms in the above $C_{1-4}$ alkyl group may be substituted by a substituent, and specific examples of the substituent include a hydroxyl group, a $C_{1-4}$ alkoxy group, a mercapto group, a $C_{1-4}$ alkylthio group, a cyano group, a halogen atom, a carboxyl group, a $C_{1-4}$ alkoxycarbonyl group, a carbamoyl group, an N—$C_{1-4}$ alkylcarbamoyl group, a formyl group, an alkylcarbonyl group, a hydroxyimino group, a $C_{1-4}$ alkoxyimino group, an amino group, a formylamino group, a $C_{1-4}$ alkylcarbonylamino group, a $C_{1-4}$ alkylcarbonylamino group (which may be substituted by a halogen atom), a carbamoyloxy group, an N—$C_{1-4}$ alkylcarbamoyloxy group, a $C_{1-4}$ alkylsulfonylamino group, a ureido group, an N—$C_{1-4}$ alkylureido group, a $C_{1-4}$ alkoxycarbonylamino group. Specific examples of the $C_{1-4}$ alkyl group substituted by the above substituent(s) include carboxylmethyl, carbamoylmethyl, hydroxymethyl, 2-hydroxyethyl, (formylamino)methyl, fluoromethyl, difluoromethyl, (hydroxyimino)methyl, dimethoxymethyl, acetoxymethyl, methoxymethyl, (R)-1-(formylamino)methyl, (S)-1-(formylamino)methyl, 2-(formylamino)ethyl, Specific examples of more preferable compounds of the invention are as follows:

(6R, 7R)-7-[(Z)-2-(5-amino-1,2,4-thiadiazol-3-yl)-2-fluoromethoxyiminoacetamido]-3-[3-(imidazo[5,1-b]thiazolium-6-yl)-1-propenyl]-3-cephem-4-carboxylate (internal salt);

(6R, 7R)-7-[(Z)-2-(5-amino-1,2,4-thiadiazol-3-yl)-2-fluoromethoxyiminoacetamido]-3-[3-(3-methylimidazo[5,1-b]thiazolium-6-yl)-1-propenyl-3-cephem-4-carboxylate (internal salt);

(6R, 7R)-7-[(Z)-2-(5-amino-1,2,4-thiadiazol-3-yl)-2-fluoro methoxyiminoacetamido]-3-[3-(3-carbamoylimidazo[5,1-b]thiazolium-6-yl)-1-propenyl]-3-cephem-4-carboxylate (internal salt); and (6R, 7R)-7-[(Z)-2-(5-amino-1,2,4-thiadiazol-3-yl)-2-fluoromethoxyiminoacetamido]-3-[3-(5-formylaminomethylimidazo[5,1-b]thiazolium-6-yl]-1-propenyl]-3-cephem-4-carboxylate (internal salt).

The compounds of the formula (I) according to the present invention may be in the form of pharmaceutically acceptable salts thereof. Examples of such salts include medically acceptable nontoxic salts. Preferable examples of a salt formed at the amino and/or imidazo[5,1-b]thiazolium-6-yl group include salts of halogen hydroacid such as hydrofluoric acid, hydrochloric acid, hydrobromic acid or hydroiodic acid; inorganic acid salts such as sulfate, nitrate, phosphate, perchlorate and carbonate; salts of carboxylic acid such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid or malic acid; salts of acidic amino acid such as aspattic acid or glutamic acid; salts of sulfonic acid such as methanesulfonic acid or p-toluenesulfonic acid; and organic acid salts such as ascorbate. Examples of a salt formed at the carboxyl group include alkaline metallic salts such as a sodium salt, a potassium salt and a lithium salt; alkaline earth metallic salts such as a calcium salt and a magnesium salt; ammonium salts; salts of an organic amine such as triethylamine, trimethylamine, diethylamine, pyridine, ethanolamine, triethanolamine, dicyclohexylamine, procaine, benzylamine, N-methylpiperidine, N-methylmorpholine or diethylaniline; and salts of basic amino acid such as lysine, arginine or histidine.

Preparation of the Compounds

The compounds of the formula (I) according to the present invention can be preferably prepared in accordance with the following scheme:

W represents a leaving group, preferably a halogen atom, or a diphenylphosphoryloxy, methanesulfonyloxy, p-toluenesulfonyloxy, trifluoromethanesulfonyloxy or acetoxy group.

The reaction of compound (II) and compound (III) in the scheme can be completed by reacting the compound (II) with an equal or excess amount of the compound (II) in a proper solvent (e.g., acetone, methyl ethyl ketone, ethyl acetate, chloroform, dichloromethane, tetrahydrofuran, dioxane, N,N-dimethylformamide, acetonitrile, hexamethylphosphoric triamide, toluene, methanol or ethanol) at a temperature of −20° C. to 50° C. for 3 to 24 hours. After the reaction is completed, the reaction solution is post-treated in a conventional manner. If necessary, the compound (IV) thus obtained is purified by column chromatography using silica gel or Sephadex LH-20, and crystallization.

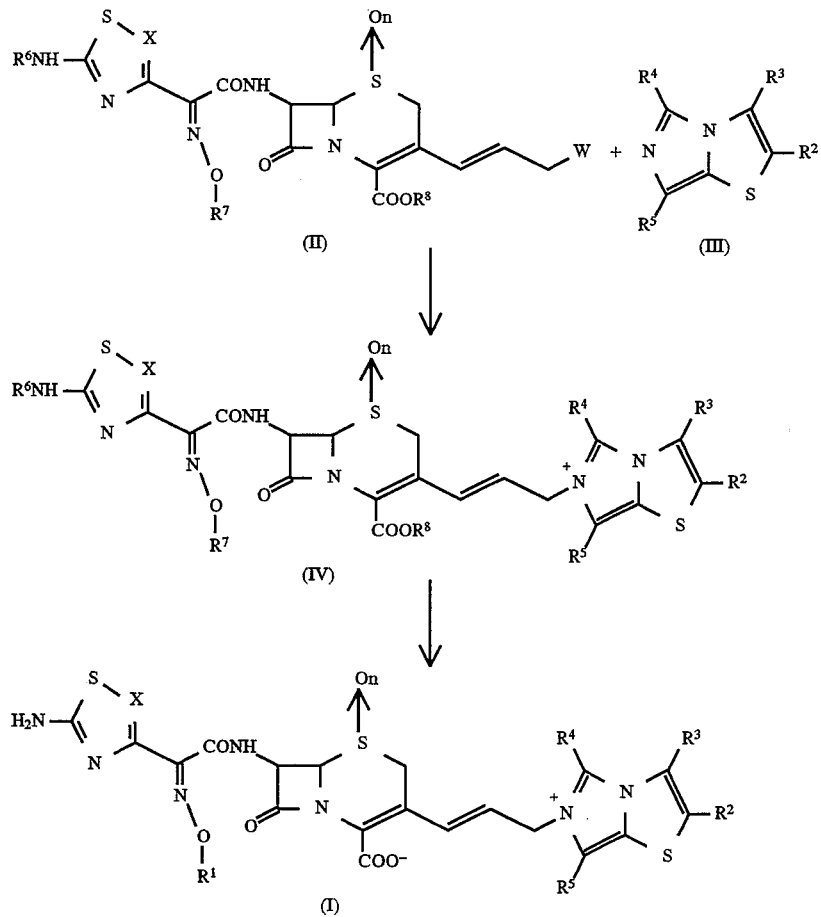

wherein X, $R^1$, $R^2$, $R^3$, $R^4$, $R^5$ and n are as defined in the formula (I), $R^6$ represents a hydrogen atom or an amino protective group (e.g., a trityl, chloroacetyl or formyl group), $R^7$ has the same meaning of $R^1$, provided that when $R^1$ has a carboxyl group, the carboxyl group may be protected by a protective group (e.g., a diphenyl, benzyl, p-methoxybenzyl, p-nitrobenzyl, tert-butyl, allyl or 2,2,2-trichloroethyl group), or represents an oxime protective group (e.g., a trityl group), $R^8$ represents a hydrogen atom or a carboxy protective group (e.g., a diphenylmethyl, benzyl, p-methoxybenzyl, p-nitrobenzyl, tert-butyl or allyl group), and In the case where both $R^6$ and $R^8$ represent a hydrogen atom, and $R^7$ and $R^1$ are the same, a compound represented by the formula (I) of the present invention can be obtained without conducting the step of deprotection, which is described below.

On the other hand, in the case where a compound (I) of the present invention can be obtained by removing the protective groups $R^6$, $R^7$ and $R^8$, the deprotection of these groups can be carried out in a conventional manner. When the protective groups $R^6$, $R^7$ and $R^8$ can be removed under the acidic condition, it is suitable to treat the compound (IV) with trifluoroacetic acid, formic acid, hydrochloric acid or the like. When any one of or all of the groups $R^6$, $R^7$ and $R^8$ can be removed under the conditions for reduction, it is proper to treat the compound (IV) by means of catalytic reduction using one of a variety of catalysts, or with a metal reducing agent such as zinc. Further, when $R^6$ is a chloroacetyl group, it can be removed by reacting the compound (IV) with one of various thioamides.

By properly adjusting the pH of the aqueous reaction solution, the compound (I) can be crystallized and precipitated. If necessary, the compound (I) may be purified and isolated by chromatography using a nonionic macroporous resin, or by gel filtration using Sephadex or the like.

The compound (II) may be prepared by a known method or a method analogous thereto. Specifically, it may be prepared in accordance with the method described in Japanese Patent Laid-Open publication No. 26447/1988 and J. Antibiot., 43(5), 533 (1990).

The compound (III) may be prepared by a known method or a method analogous thereto. Specifically, it may be prepared in accordance with the method described in Liebigs Ann. Chem., 679, 144 (1964).

Use of the Compounds/Pharmaceutical Compositions

The compounds according to the present invention have potent antibacterial activity effective against a wide variety of Gram-positive and Gram-negative bacteria. In particular, they are effective against beta-lactamase-producing bacteria. Moreover, their toxicity is low, and their absorbability is high.

Therefore, the compounds according to the present invention can be used for the treatment of infectious diseases in animals including humans, caused by various pathogenic fungi.

A pharmaceutical composition comprising as an active ingredient a compound of the present invention or a pharmaceutically acceptable salt thereof can be administered either orally or parenterally (e.g., intravenous injection, intramuscular injection, subcutaneous administration, rectal administration, percutaneous administration) to humans or animals other than humans.

The pharmaceutical composition comprising as an active ingredient a compound of the present invention may be made into a preparation suitable for an administration route to be adopted. Specifically, it may be made into any of the following preparations: an injection for intravenous or intramuscular injection; a capsule, a tablet, a granule, a powder, a pill or a troche for oral administration; a parenteral preparation; and an oily or aqueous suppository.

The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose or a salt thereof, gum arabic, polyethylene glycol, syrup, vaseline, glycerol, ethanol, propylene glycol, citric acid, sodium chloride, sodium sulfite and sodium phosphate.

The dosage of the compound of the present invention is properly determined in consideration of the regimen, the age and sex of a patient, and the conditions of disease. However, for the treatment of infectious disease, approximately 100 mg to 4000 mg, preferably 500 mg to 2000 mg of the compound is generally administered per day for adult human, desirably at one time or several times.

The present invention will now be explained more specifically by referring to the following examples. However, the present invention is not limited by these examples.

EXAMPLE 1

(6R, 7R)-7-[(Z)-2-(5-amino-1,2,4-thiadiazol-3-yl)-2-fluoromethoxyiminoacetamido]-3-[3-(imidazo[5,1-b]-thiazo lium-6-yl)-1-propenyl]-3-cephem-4-carboxylate (internal salt)

To 356 mg of diphenylmethyl (6R, 7R)-7-[(Z)-2-(5-tritylamino-1,2,4-thiadiazol-3-yl)-2-fluoromethoxyiminoacetamido]-3-(3-chloro-1-propenyl)-3-cephem-4-carboxylate in acetone (4 ml), 85 mg of sodium iodide was added, and the mixture was stirred for 1 hour at room temperature. The acetone was distilled off under reduced pressure. To the residue were added 10 ml of ethyl acetate, 5 ml of 20% sodium chloride solution and 5 ml of 5% sodium thiosulfate, and the mixture was vigorously stirred and then separated. The organic layer was dried over anhydrous magnesium sulfate, and evaporated under reduced pressure to give (6R, 7R)-7-[(Z)-2-(5-tritylamino-1,2,4-thiadiazol-3-yl)-2-fluoromethoxyiminoacetamido)-3-(3-iodo-1-propenyl]-3-cephem-4-carboxylate.

The iodide derivative was dissolved in 4 ml of N,N-dimethylformamide, 60 mg of imidazo[5,1-b]thiazole was added thereto, and the mixture was stirred for four hours at room temperature. To the reaction mixture, 2.720 g of sodium trifluoroacetate in 16 ml of water was added. The precipitate was collected by filtration and then dried.

To the precipitate, 2 ml of anisole was added and then 4 ml of trifluoroacetic acid was added with ice-cooling, and the mixture was stirred for one hour at room temperature. Under ice cooled, the reaction mixture was added dropwise to 2 ml of iso-propylether, and the precipitate was then collected by filtration and dried.

The precipitate was suspended in 3 ml of water, and pH of the mixture was adjusted to 7–8 with saturated sodium hydrogencarbonatel The mixture was purified by Diaion HP-20 (5% and 10 % aqueous solution of acetone) and then Sephadex LH-20 (50% aqueous solution of methanol). The product was freeze-dried to give 69 mg of the title compound. (Yield: 31%) NMR (D$_2$O) δ(HDO=4.80): 3.67 (2H, s), 5.10 (2H, d, J=6 Hz), 5.28 (1H, d, J=5 Hz), 5.86 (2H, d, J=54 Hz), 5.86 (1H, d, J=5 Hz), 6.10 (1H, dt, J=5 Hz, 16 Hz), 6.84 (1H, d, J=16 Hz), 7.53 (1H, d, J=5 Hz), 7.68(1H, s), 7.93 (1H, d, J=5 Hz), 9.28 (1H, s).

EXAMPLE 2

(6R, 7R)-7-[(Z)-2-(5-amino-1,2,4-thiadiazol-3-yl)-2-fluoromethoxyiminoacetamido]-3-[3-(3-methylimidazo [5,1-b]thiazolium-6-yl)-1-propenyl]-3-cephem-4-carboxylate (internal salt)

The title compound (82 mg) was obtained from diphenylmethyl (6R, 7R)-7-[(Z)-2-(5-tritylamino-1,2,4-thiadiazol-3-yl)-2-fluoromethoxyiminoacetamido)-3-(3-chloro-1-propenyl)-3-cephem-4-carboxylate (356 mg) and 3-methylimidazo[5,1-b]thiazole (66 mg) in the same manner as in Example 1. (Yield: 35%) NMR (D$_2$O) δ(HDO=4.80): 2.49 (3H, s), 3.67 (2H, s), 5.09 (2H, d, J=6 Hz), 5.28 (1H, d, J=5 Hz), 5.85 (2H, d, J=54 Hz), 5.86 (1H, d, J=5 Hz), 6.10 (1H, dt, J=5 Hz, 16 Hz), 6.84 (1H, d, J=16 Hz), 7.11 (1H, s), 7.65 (1H, s), 9.27 (1H, s).

EXAMPLE 3

(6R, 7R)-7-[(Z)-2-(5-amino-1,2,4-thiadiazol-3-yl)-2-fluoro methoxyiminoacetamido]-3-[3-(3-carbamoylimidazo [5,1-b]thiazolium-6-yl)-1-propenyl]-3-cephem-4-carboxylate (internal salt)

The title compound (83 mg) was obtained from diphenylmethyl (6R, 7R)-7-[(Z)-2-(5-tritylamino-1,2,4- thiadiazol-3-yl)-2-fluoromethoxyiminoacetamido)-3-(3-chloro-1-propenyl)-3-cephem-4-carboxylate (356 mg) and 3-carbamoylimidazo[5,1-b]thiazole (80 mg) in the same manner as in Example 1. (Yield: 34% NMR (D$_2$O) δ(HDO=4.80): 3.67 (2H, s), 5.13 (2H, d, J=6 Hz), 5.28 (1H, d, J=5 Hz), 5.86 (2H, d, J=54 Hz), 5.86 (1H, d, J=5 Hz), 6.11 (1H, dt, J=5 Hz, 16 Hz), 6.84 (1H, dt J=16 Hz), 7.77 (1H, s), 8.38 (1H, s), 9.67 (1H, s).

EXAMPLE 4

(6R, 7R)-7-[(Z)-2-(5-amino-1,2,4-thiadiazol-3-yl)-2-fluoro methoxyiminoacetamido]-3-[3-(5-formylaminomethylimidazo[5,1-b]thiazolium-6-yl]-1-propenyl]-3-cephem-4-carboxylate (internal salt)

The title compound (44 mg) was obtained from diphenylmethyl (6R, 7R)-7-[(Z)-2-(5-tritylamino-1,2,4-thiadiazol-3-yl)-2-fluoromethoxyiminoacetamido)-3-(3-chloro-1-propenyl)-S-cephem-4-carboxylate (356 mg) and 5-formylaminomethylimidazo[5,1-b]thiazole (87 mg) in the same manner as in Example 1. (Yield: 18%) NMR (D$_2$O) ←(HDO=4.80): 3.65 (2H, s), 4.98 (2H, s), 5.15 (2H, d, J=6 Hz), 5.26 (1H, d, J=5 Hz), 5.85 (2H, d, J=54 Hz), 5.85 (1H, d, J=5 Hz), 6.05 (1H, dt, J=5 Hz, 16 Hz), 6.69 (1H, d, J=16 Hz), 7.58 (1H, d, J=5 Hz), 7.68 (1H, s), 8.04 (1H, d, J=5 Hz), 8.18 (1H, s).

PREPARATION EXAMPLES

Preparation for Injection

A pharmaceutical composition containing a compound according to the present invention is aseptically charged into vials so that each vial may contain 1000 mg (potency) of the compound of the invention.

Capsulated Preparation

Compound of the present Invention 250 parts (potency)
Lactose 60 parts (potency)
Magnesium stearate 5 parts (potency)

The above ingredients are homogeneously mixed, and the mixture is charged into capsules so that each capsule may contain 250 mg (potency) of the compound of the invention.

Soft Capsulated Preparation for Rectal Administration

Olive oil 160 parts
Polyoxyethylene lauryl ether 10 parts
Sodium hexamethaphosphate 5 parts To a base which is a homogeneous mixture of the above-ingredients is added 25 parts (potency) of a compound according to the present invention, and the mixture was homogeneously mixed. The resulting mixture is charged into soft capsules for rectal administration so that each capsule may contain 250 mg (potency) of the compound of the invention.

Antibacterial Activity Test

The antibacterial activity of the compounds according to the present invention was demonstrated by the minimum inhibitory concentrations (MIC) of the compounds against various bacteria, measured by a conventional two-fold dilution method. The test was carried out in the following manner: 10$^6$ CFU/ml of a bacterium to be tested was inoculated on a Medium N for disc susceptibility test (manufactured by Nissui Pharmaceutical Co., Ltd.), and cultivated at 35° C. for 18 to 20 hours. The results are as shown in the following table.

| Test strain | MIC (μg/ml) Example No. of Test Compound | | | |
| --- | --- | --- | --- | --- |
| | 1 | 2 | 3 | 4 |
| S. aureus 209P JC-1 | 0.20 | 0.20 | 0.20 | 0.39 |
| S. epidermidis ATCC14990 | 0.10 | 0.20 | 0.20 | 0.20 |
| E. faecalis W-73 | 12.5 | 12.5 | 12.5 | 12.5 |
| E. coli NIHJ JC-2 | <0.025 | 0.05 | 0.05 | <0.025 |
| K. pneumoniae PC1602 | 0.05 | 0.05 | 0.05 | <0.025 |
| P. vulgaris GN76 | 0.10 | 0.10 | 0.10 | 0.10 |
| M. morganii 1510/S-1 | <0.025 | <0.025 | <0.025 | <0.025 |
| C. freundii GN346/16 | 0.05 | 0.05 | 0.05 | <0.025 |
| R. cloacae G-0008 | 0.05 | 0.05 | 0.05 | 0.05 |
| S. marcescens No.1 | 0.05 | 0.05 | 0.05 | 0.05 |
| P. auruginosa E-2 | 12.5 | 25 | 12.5 | 12.5 |

What is claimed is:

1. A cephem derivative represented by the formula (I):

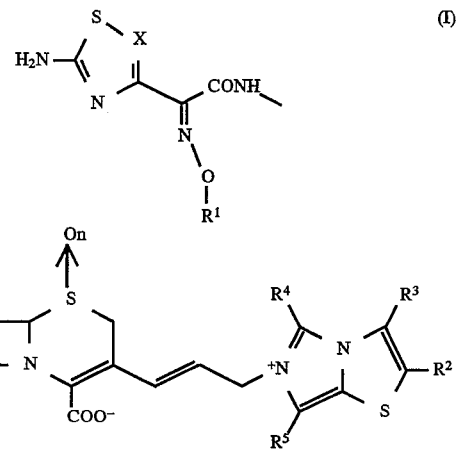

wherein

X represents CH or N,

R$^1$ represents hydrogen; C$_{1-4}$ alkyl in which one or more hydrogen atoms may be substituted by halogen, hydroxyl, carboxyl, C$_{1-4}$ alkoxycarbonyl, carbamoyl, N—C$_{1-4}$ alkylcarbamoyl, cyano, amino or C$_{1-4}$ alkylamino group; C$_{2-4}$ alkenyl; C$_{2-4}$ alkynyl; or C$_{3-6}$ cycloalkyl, R$^2$, R$^3$, R$^4$ and R$^5$, which may be the same or different, represent hydrogen; C$_{1-4}$ alkoxy; C$_{1-4}$ alkylthio; cyano; carboxyl; C$_{1-4}$ alkoxycarbonyl; carbamoyl; N—C$_{1-4}$ alkylcarbamoyl; formyl; amino in which one or more hydrogen atoms may be substituted by formyl, C$_{1-4}$ alkylcarbonyl or C$_{1-4}$ alkylsulfonyl; halogen; C$_{1-4}$ alkyl in which one or more hydrogen atoms may be substituted by hydroxyl, C$_{1-4}$ alkoxy, mercapto, C$_{1-4}$ alkylthio, cyano, halogen, carboxyl, C$_{1-4}$ alkoxycarbonyl, carbamoyl, N—C$_{1-4}$ alkylcarbamoyl, formyl, alkylcarbonyl, hydroxyimino, C$_{1-4}$ alkoxyimino, amino, formylamino, C$_{1-4}$ alkylcarbonylamino, C$_{1-4}$ alkylcarbonylamino (which may be substituted by a halogen atom), carbamoyloxy, N—C$_{1-4}$ alkylcarbamoyloxy, C$_{1-4}$ alkylsulfonylamino, ureido, N—C$_{1-4}$ alkylureido, C$_{1-4}$ alkoxycarbonylamino or imino C$_{1-4}$ alkylamino; C$_{3-6}$ cycloalkyl; C$_{2-4}$ alkenyl; or C$_{2-4}$ alkynyl, any two of R$^2$, R$^3$, R$^4$ and R$^5$ may form C$_{3-6}$ alkylene, where one or more methylene groups in this alkylene group may be substituted by —NH—, —O—, —S— or —CO—, and n is 0 or 1; and a pharmaceutically acceptable salt thereof.

2. The compound according to claim 1, wherein $R^1$ is $C_{1-4}$ alkyl which may be substituted by halogen.

3. The compound according to claim 1, wherein $R^2$, $R^3$, $R^4$ or $R^5$ represents $C_{1-4}$ alkyl, carbamoyl or formyl.

4. The compound according to claim 1 selected from;

(6R, 7R)-7-[(Z)-2-(5-amino-1,2,4-thiadiazol-3-yl)-2-fluoromethoxyiminoacetamido]-3-[3-(imidazo[5,1-b]thiazolium-6-yl)-1-propenyl]-3-cephem-4-carboxylate (internal salt);

(6R, 7R)-7-[(Z)-2-(5-amino-1,2,4-thiadiazol-3-yl)-2-fluoromethoxyiminoacetamido]-3-[3-(3-methylimidazo[5,1-b]thiazolium-6-yl)-1-propenyl]-3-cephem-4-carboxylate (internal salt);

(6R, 7R)-7-[(Z)-2-(5-amino-1,2,4-thiadiazol-3-yl)-2-fluoro methoxyiminoacetamido]-3-[3-(3-carbamoylimidazo[5,1-b]thiazolium-6-yl)-1-propenyl]-3-cephem-4-carboxylate (internal salt); and (6R, 7R)-7-[(Z)-2-(5-amino-1,2,4-thiadiazol-3-yl)-2-fluoro methoxyiminoacetamido]-3-[3-(5-formylaminomethylimidazo[5,1-b]thiazolium-6-yl)-1-propenyl]-3-cephem-4-carboxylate (internal salt).

5. A pharmaceutical composition comprising the compound according to any one of claims 1 to 4 together with a pharmaceutically acceptable carrier.

6. A pharmaceutical composition according to claim 5 used for an antibacterial agent.

7. A method for treating infectious diseases comprising administering any one of claims 1 to 4 to a mammal including human.

8. Use of any one of claims 1 to 4 together with a pharmaceutically acceptable carrier for preparing an antibacterial agent.

* * * * *